United States Patent [19]

Bird et al.

[11] Patent Number: 4,464,482
[45] Date of Patent: Aug. 7, 1984

[54] THREE DIMENSIONAL INTERSTITIAL CATALYST SUPPORT AND ITS MANUFACTURE

[75] Inventors: Alfred J. Bird, Hounslow; Frank King, Reading, both of England

[73] Assignee: Johnson Matthey Public Limited Company, London, England

[21] Appl. No.: 438,733

[22] Filed: Nov. 3, 1982

Related U.S. Application Data

[63] Continuation-in-part of Ser. No. 324,485, Nov. 24, 1981, abandoned.

[30] Foreign Application Priority Data

Nov. 27, 1980 [GB] United Kingdom ............... 8038020
Mar. 18, 1981 [GB] United Kingdom ............... 8108392
Apr. 21, 1981 [GB] United Kingdom ............... 8112331
Sep. 9, 1981 [GB] United Kingdom ............... 8127289

[51] Int. Cl.³ .................. B01J 23/38; B01J 23/48; B01J 35/00
[52] U.S. Cl. .................. 502/325; 502/344; 502/347; 502/527
[58] Field of Search .................. 252/477 R; 502/325, 502/344, 347, 527

[56] References Cited

U.S. PATENT DOCUMENTS

| | | | |
|---|---|---|---|
| 2,750,346 | 6/1956 | Sherwood | 252/477 R |
| 3,362,783 | 1/1968 | Leak | 252/447 R |
| 3,874,645 | 4/1975 | Aguinet et al. | 267/112 |
| 3,956,192 | 5/1976 | Nicolai | 252/477 R |
| 4,293,447 | 10/1981 | Inaba et al. | 252/477 R |
| 4,363,753 | 12/1982 | Bozon et al. | 252/477 R |

FOREIGN PATENT DOCUMENTS

| | | |
|---|---|---|
| 2238520 | 2/1975 | France . |
| 2248875 | 5/1975 | France . |
| 2395070 | 1/1979 | France . |
| 1466465 | 3/1977 | United Kingdom . |
| 2029720 | 3/1980 | United Kingdom . |
| 2034596 | 6/1980 | United Kingdom . |
| 2036585 | 7/1980 | United Kingdom . |

*Primary Examiner*—W. J. Shine
*Attorney, Agent, or Firm*—Cushman, Darby & Cushman

[57] ABSTRACT

A three dimensional interstitial catalyst support and a catalyst system comprising the support for use in (especially pressure-sensitive) surface reactions involving disturbed fluid flow, especially trickle feed three phase reactions such as the hydrogenation of crotonaldehydes or butyraldehyde. The support comprises a three dimensional self-supporting form-stable interstitial structure composed of five or more superimposed intermeshing layers of knitted cloth and the volume of the interstices in the structure is from 60 to 98 (preferably at least 85) % of the volume of the structure. The combination of the use of intermeshing knitted wire, form-stability and an open structure allows disturbances comprising components of motion transverse to the general flow of the fluid through the support to be imparted by the catalyst system with less risk of blockages, flooding or damage by attrition and hence less need to increase pressure during a reaction which is undesirable in pressure sensitive reactions. Also a method for making the structures by rolling up knitted wire cloth, compressing it to the pre-determined volume and annealing.

15 Claims, 10 Drawing Figures

THREE DIMENSIONAL INTERSTITIAL CATALYST SUPPORT AND ITS MANUFACTURE

This application is a continuation in part of co-pending application Ser. No. 324,485 (filed on Nov. 24, 1981), now abandoned the contents of which are herein incorporated by reference.

BACKGROUND TO THE INVENTION

1. Field of the Invention

This invention relates to a three dimensional interstitial catalyst support and to a three dimensional interstitial catalyst system comprising the support which is suitable for use in catalysing chemical (especially pressure-sensitive) reactions which require disturbed flow having components of motion transverse to the general flow of fluid through the support to be imparted to one or more liquids. The support and catalyst system are especially suitable for use in trickle feed three phase rections in which a liquid is trickle fed and a gas is fed into a reaction zone packed with an interstitial solid catalyst system. Trickle feed three phase reactions are used for example in the hydrogenation of crotonaldehyde or butyraldehyde. The invention also relates to a convenient method for making the support and to a process using the catalyst system comprising the support.

Efficient performance of a liquid/solid phase catalysed reaction requires disturbed flow of the fluid so as to ensure good contact between the liquid and the solid catalyst. In particular, in a trickle feed three phase reaction the liquid should thoroughly wet the solid otherwise only a low conversion of liquid to product occurs and also if two or more products are possible, then the selectivity towards the preferred product may be reduced.

2. Description of the Prior Art

To ensure good selectivity and conversion, the catalyst systems hitherto employed have comprised elements such as pellets, sintered powders, closely woven or closely knitted two dimensional wire screens or narrow bore tubes optionally stuffed with steel wool to increase the obstructiveness of the elements. Such elements pack closely so as to obstruct flows mechanically and so impart a transverse component to flows which would otherwise be mainly longitudinal of an elongated catalyst system. Despite close packing, such systems are interstitial in that interstices are defined by the adjacent packed pellets, or by the weave or knit of a screen or by the bore and packing arrangement of tubes. In practice the volume of the interstices is no more than 30% of the volume of the whole catalyst system so as to ensure adequate obstruction.

Elements used in such close packed catalyst systems comprised either unsupported catalyst component or catalyst component absorbed into supports such as zinc oxide, alumina, magnesia, silica or silicates such as asbestos. However, with both types of element attrition seems to occur during use and the interstices become increasingly blocked by trapped particles so that increasing pressure gradients become necessary to maintain the reaction. In pressure-sensitive reactions, increased pressure often results in decreased selectivity and hence increased amounts of by-product. Eventually the reaction ceases to be worthwhile. For example in hydrogenation of crotonaldehyde or butyraldehyde, blockages and consequent necessary increases in pressure can limit the commercially useful life of a pelletised copper chromite catalyst system to as little as three days.

Pelletised catalyst systems present an additional general problem in that it is often necessary to shovel pellets manually around areaction zone in order to achieve the required pattern of interstices.

Closely packed catalyst systems present a specific problem when used in trickle feed three phase reactions. They are vulnerable to the interstices flooding (ie becoming filled exclusively with liquid). A reaction involving liquid and gaseous phases is impossible in flooded areas (neglecting any minor reaction which may be possible between liquid and dissolved gas). Another problem arising from flooded interstices is that flooded interstices canalise the gas into exclusively gaseous flows causing it to pass through the system without mixing and reacting with the liquid.

Interstitial catalyst systems having open metal supports have been proposed for use in the purification of exhaust gases coming from gasoline engines in motor vehicles. Typically such supports comprise a cylindrical so-called honeycomb structure containing spiral layers made by rolling up a pair of superimposed layers, one layer being relatively impermeable (for example a layer of stainless steel foil) and the other layer being a material which defines open interstices. As exhaust gases pass longitudinally through the support, the relatively impermeable layer inhibits radial flow so minimising eddying which would hinder escape of exhaust gases from the engine. Such catalyst systems are suitable for promoting gaseous reactions, but their suppression of radial flow makes them unsuitable for use in reactions involving liquids, especially trickle feed reactions where the imposition of transverse flow to liquids is essential.

SUMMARY OF THE INVENTION

It is among the objectives of this invention to reduce or overcome some of the problems associated with close packed three dimensional interstial catalyst systems. Another object is to provide a convenient method for making a catalyst support structure which reduces such problems. A further object is to improve the selectivities and/or conversions which can be achieved in solid phase catalysed reactions of the type requiring transverse flow to be imparted to one or more liquids passing longitudinally into a catalyst. By "conversion" is meant the % by weight of an organic reactant which is converted to product so that "conversion" is a measure of the proportion of a reactant which is able to react under the conditions chosen for the reaction. By "selectivity" is meant the % by weight of product which is required product as opposed to by-product. For example, in the case of trickle feed three phase reactions it is a particular objective to improve selectivity and conversion by imposing transverse flow in order to reduce the risk of flooding and gas canalisation in the catalyst system. Accordingly this invention provides a three dimensional interstitial catalyst support suitable for use in a fluid/interstitial solid catalysed reaction wherein the support comprises a three dimensional wire interstitital structure composed of five or more superimposed intermeshing two dimensional layers of knitted wire interstitial cloth in which the volume of the interstices in the structure is from 60 to 98% e.g. 70 to 95%, of the total volume of the structure and in which the surface of the wire is provided with an oxide moiety suitable for bonding a catalyst component to the wire and which holds together adjacent portions of the layers of cloth to make the structure more form-stable.

According to the invention, the interstices of the support are defined by adjacent portions of metal oxide- or moiety-bearing wire.

It has been discovered that when a fluid flows through a catalyst system comprising a support of such open structure, the structure is less vulnerable to attrition and consequent blockage and yet despite the openness of the structure, the intermeshing layers of knitted cloth nevertheless still generate a high level of disturbance. In particular in a trickle feed three phase reaction, the risk of gas canalisation is not merely reduced but is often eliminated. Decreased vulnerability to blockage results in a catalyst system which is less likely to need increasing pressure gradients to maintain the reaction and pressure gradients as low as $1 \times 10^{-3}$ pascals have been maintained. Decreased vulnerability to blockage also means that catalyst systems comprising the supports have longer useful lives. In particular, trickle feed reactions can be operated for long periods without a need to flush gas through the system to clear out solid particles, gaseous by-products or impurities. This in turn means that if a gas is consumed in the reaction, it is often sufficient just to feed the gas into the catalyst system without having to pass much (if any) of it through the system which is advantageous in that compressor capacity for re-cycling gas is either substantially decreased or not needed.

The disturbance comprises imparting a component of motion to the liquid which is transverse to the general direction of flow of the fluid through the support. It is probable that in the case of a slowly flowing liquid reactant, most of this disturbance is imparted by surface tension forces generated as different portions of a quantity of fluid are induced to flow along different but closely adjacent intermeshing portions of wire. Accordingly it is possible to use the catalyst system with slow liquid flow rates. It is not until speed of flow of the liquid increases, that there is any significant possibility of a mechanical deflecting effect created as liquid collides with obstructing lengths of wire. Preferred flow rates for liquid reactants are 10 to 50 (especially 15 to 50) cm$^3$ per 100 cm$^3$ of catalyst system.

Better contact between fluid (especially gas) and solid is achieved if the wire is non-circular in cross-section. Suitable cross-sections may be oblate (for example at least approximately elliptical) or at least approximately rectangular. A suitable cross-section may be obtained by rolling a cylindrical wire of diameter 0.15 to 0.7 mm. It is possible that turbulence in gaseous fluids increases if the wire is provided with one or more longitudinally extended edges. Preferably the maximum transverse dimension of the wire should be from 0.1 to 0.7 mm. The wire may be unitary or composes or a plurality of strands arranged side by side. A stranded wire is more easily knitted but is less form-stable.

Many factors influence the amount of disturbance imparted to a liquid flowing through the catalyst system. However, for good disturbance, it is preferred that the maximum dimension of an interstice should be less than 10 times the maximum transverse dimension of the wire which defines it. It is also preferrd that adjacent interstices should belong to different families of interstices wherein the direction of the shortest pathway through an interstice of one family is inclined to the direction of the shortest pathway through an interstice of any other family. This ensures that liquid flowing through interstices of different families must follow a tortuous and therefore more disturbed route. It also ensures that adjacent lengths of wire are mutually inclined and usually intercrossing.

The wire may be made from any adequately corrosion-resistant malleable metal, for example austenitic stainless steels, nickel/chromium alloys or ferritic steels containing aluminium. Preferably the steel contains at least 10% by weight of chromium. For some purposes aluminium wire may be used.

A convenient method for making the three dimensional wire interstitial structure comprises
(a) arranging five or more layers of interstitial knitted wire cloth one on top of another,
(b) compressing the arrangement of layers to a predetermined volume,
(c) annealing the compressed layers so that they become stable in a compressed state and
(d) at some stage after step (a), securing the layers to produce a form-stable structure.

The use of the compression step permits accurate control of the volume of the interstices. The arrangement of five or more superimposed layers is easily made by rolling up a length of the cloth and the outer loose end of the cloth is secured (preferably knotted) to the remainder of the roll to give form-stability by preventing unrolling. Knitted cloths are pliable and so are well suited to the compression step.

To convert the structure into a catalyst support, the oxide moiety is provided on the wire. The moiety may be generated in situ and/or it may be applied using an external source. For example if the wire is made from an alloy containing a component (for example chromium or aluminium) which oxidises in preference to other components, then the oxide moiety may be generated in situ by exposing the wire to controlled oxidising conditions. For example the wire may be heated in oxygen or air at from 800° to 1100° C. and preferably 1000° C. Under such conditions, a suitable preferentially oxidisable component will form a very tenacious refractory oxide on the wire.

If it is preferred to provide the oxide moiety from a totally external source, this may be done by coating (preferably dip- or spray-coating) the wire with a dispersion (for example a paste, slurry or suspension) of a refractory oxide of a metal or a precursor which can be converted to the oxide by firing. The coating is then dried and fired to bond the oxide to the wire. A refinement of the method comprises chemically depositing onto the wire a precursor which is a salt or hydroxide. For example gibbsite (an aluminium hydroxide) may be deposited from a saturated solution of sodium aluminate and then fired to form a layer of γ-alumina. Such coating techniques are known as "washcoating". Preferably the oxide moiety should be provided on the wire in amounts of from 0.05 to 0.5 g (preferably 0.1 to 0.3 g) per gram of wire support. Usually this means that the thickness of a layer of moiety is from 4 to 16 (preferably from 8 to 12) μm.

A particularly useful structure comprises wire containing a preferentially oxidisable component which has been oxidised to provide a tenacious layer of refractory oxide moiety and then subsequently washcoated to produce a further layer of refractory moiety. Such double layered moieties are especially resistant to attrition.

Preferably the non-metallic oxide moieties on adjacent (preferably intercrossing) portions of wire are allowed to bond together during their formation so that the wire structure becomes reinforced by a network of cross-links which make it very form-stable and resistant to attrition. Cross-links also assist in causing a quantity of liquid to divide and flow along the different adjacent portions of the cross-linked structure and so they enhance the wetting of the catalyst system by the liquid.

The form-stability of the catalyst supports of this invention allows them to be positively located in a reaction zone and so avoids the need for manual shovelling to ensure an adequate pattern of interstices. In particular the form stability of supports enables them to be mounted (with their axes verticle) in reactor columns to a height of 3 m without the use of supporting frames. This invention also provides a supported interstitial catalyst system comprising a catalyst component characterised in that the catalyst component is supported on an interstitial wire structure according to this invention. The catalyst component may be applied to the support by means of conventional techniques for depositing catalysts onto solid supports. For example a dispersion (preferably a solution) of the catalyst component or its precursor may be coated onto the moiety and where necessary dried and fired. Typical catalyst components comprise metals (or their compounds) of Groups 8 and 1b of the Periodic Table as published in the front inside cover of the 60th edition of the "Handbook of Chemistry and Physics" edited by R. C. Weast and published in 1979 by CRC Press Incorporated of Boca Raton, Fla. (The contents of this front inside cover are herein incorporated by reference). The supports are especially beneficial when used with catalyst components comprising one or more precious metals such as gold, silver or metals of the platinum group namely ruthenium, rhodium, palladium, osmium, iridium and platinum. The benefit arises because the supports comprise an inner metal region which is impermeable and so wastage by absorption of expensive catalyst component into inaccessible inner regions of the support is avoided.

Precious metal catalyst components may be applied to the support by immersing the support in a solution of a compound of the metal (for example aqueous solutions of ruthenium acetate or potassium palladium nitrite ie $K_2Pd(NO_2)_4$), then removing the support from the solution and drying and firing to liberate the metal from its compound. Typical loadings of catalyst are from 0.00025 to 0.1 (preferably 0.0005 to 0.05) g per gram of catalyst support.

An alternative method for applying catalyst components which are metal oxides comprises providing an oxide moiety on the wire and then treating the oxide moiety with metal compounds which under the conditions of the treatment convert at least some of the oxide to an oxide of the treating metal. For example, if the wire is made from a metal alloy containing chromium, a chromium oxide moiety may be generated in situ, treated with copper nitrate and chromic acid and then pre-reduced with hydrogen to create a copper chromite catalyst component which is active in catalysing the hydrogenation of crotonaldehyde to butyraldehyde.

This invention also provides a method for increasing the selectivity and/or conversion in a process comprising fluid/interstitial solid catalysed reaction (especially an exothermic reaction) wherein the method comprises flowing one or more fluids (which may be reactants or dispersants) into an interstitial catalyst system which imparts disturbance to the flowing fluids wherein the catalyst system comprises a catalyst component carried on a support according to this invention. Preferably the support comprises lengths of wire inclined to the general direction of flow of fluid through the catalyst system. For optimum efficiency, the catalyst system should make a close fit in a reaction chamber. For example cylindrical catalyst systems are usually loaded into close-fitting cylindrical reactor columns. Alternatively the wire structures can be compressed so as to have cross-sections which fit closely together. For example they may have rectangular, triangular or hexagonal cross-sections. Some of them may be tailored to fill particulr gaps such as those left when square section structures are loaded into circular section columns. If necessary a circular reactor column may be blanked off using flat sheets in order to define a reaction chamber of square cross-section. Frequently the economics of a process allows tolerance of a small loss of conversion efficiency arising from less than total occupation of the reaction chamber by the interstitial catalyst system.

The method confers a wide versatility on the procedure for performing three phase chemical reactions by means of interstitial catalyst systems. Particularly high percentage selectivities and percentage convesions can be achieved in trickle feed three phase reaction procedures. Trickle feed reactions are especially suited to hydrogenations, oxidations and hydrogenolyses of oxo compounds, unsaturted (including aromatic unsaturated) compounds and hydroxy compounds. The method may be performed using co- or counter-current flows. The open structure of the catalyst support also enables tricle feed phase reactions to be performed using fluids contaminated with particles which hitherto would have blocked an interstitial solid catalyst. For this reason the method is of special value for use with solvents containing particulate matter as are sometimes used in coal liquefaction processes.

BRIEF DESCRIPTION OF THE DRAWINGS

The invention is illustrated by the preferred three dimensional catalyst support comprising the three dimensional interstitial knitted wire structure described as follows with reference to FIGS. 1 to 7 of the drawings. A non-knitted wire structure used in comparative Example C is described with reference to FIGS. 8, 9 and 10 of the drawings. In the drawings.

FIG. 1 shows a piece of two dimensional interstitial knitted wire cloth 1 composed of looped adjacent intercrossing portions such as 2a, 2b and 2c which are interconnected end to end to constitute looped wire 2. Each looped portion such as 2a, 2b and 2c is interknitted with an adjacent looped portion such as 3a, 3b and 3c of similarly looped wire 3. Pairs of interknitted portions such as 2a and 3a define a family of interstices 4a, 4b and 4c.

FIG. 2 shows a compressed three dimensional interstitial wire structure 5 made by spirally rolling up a two dimensional length of the cloth 1 into a firm three dimensional interstitial self-supporting roll (not shown) comprising at least five layers of superimposed layers (for example 10a, 10b and 10c), and then securing the outer loose end 6 by knots 7 to the remainder of the roll to make the roll form-stable by preventing unrolling, then compressing the roll radially inwardly to impart a pre-determined volume to the interstices and finally annealing the compressed roll to render it stable as structure 5. In structure 5, the family of interstices 4a, 4b and 4c are circumferentially disposed and the shortest pathway through them lies in a direction extending radially of structure 5. Structure 5 also comprises other familes 9a, 9b and 9c of adjacent interstices defined by intermeshing of opposed looped portions in layers 10a, 10b and 10c of rolled-up structure 5. (For clarity, the intermeshing between layers 10a, 10b and 10c is not shown). Familes 9a, 9b and 9c extend radially of structure 5 and the direction of the shortest pathway through their interstices is longitudinal of structure 5. Hence the directions of the shortest pathways through each of the interstices of 9a, 9b and 9c are orthogonal to the directions of the shortest pathways through each of interstices 4a, 4b and 4c.

FIG. 3 shows wire 11 used in making cloth 1. Wire 11 is made by rolling a cylindrical wire 12 (shown in ghose lines) so as to produce an approximately rectangular cross-section provides a high surface area and so promotes good contact between fluid and solid.

Figure 4:
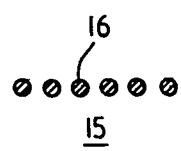
FIG. 4 is a section of a wire comprising strands.

A similar effect can be obtained by substituting wire 11 by wire 15 (shown in FIG. 4) which consists of a plurality of fine strands 16 arranged side by side.

Figure 5:
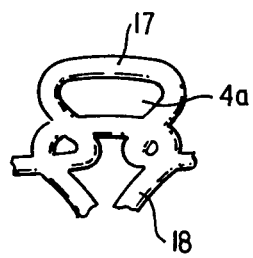
FIG. 5 is a plan (shown on a larger scale) of a piece of moiety-bearing catalyst support.
Figure 6:
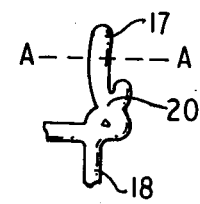
FIG. 6 is a side elevation of the piece shown in FIG. 5.
Figure 7:
FIG. 7 is a section on a larger scale taken on line A—A of FIG. 6.

FIGS. 5 and 6 show two looped portions 17 and 18 of catalyst support made by providing a coating 19 (shown in FIG. 7) of non-metallic moiety on the wire structure 5. In zone 20 where looped portions 17 and 18 intercross, coating 19 serves to bond together and crosslinked portions 17 and 18 creating highly form-stable catalyst support.

Figure 8:
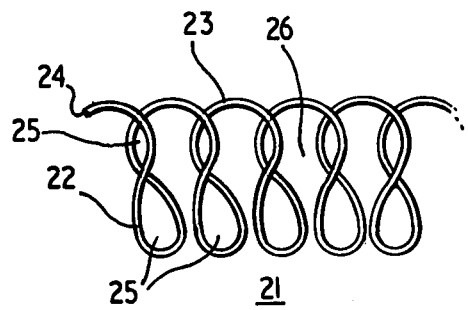
FIG. 8 is a side elevation of an element of the non-knitted wire structure used in Comparative Example C.
Figure 9:
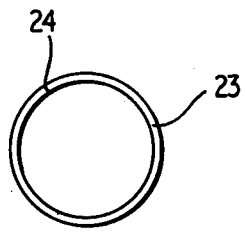
FIG. 9 is an end elevation of the element shown in FIG. 8.
Figure 10:
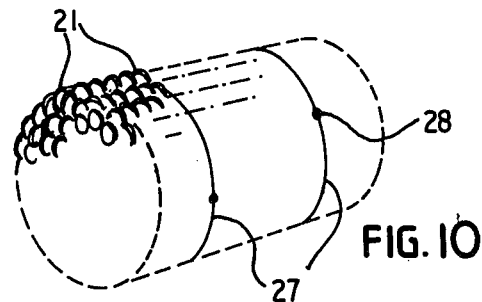
FIG. 10 is a diagrammatic perspective view on a small scale of a wire structure comprising a bundle of the elements shown in FIG. 10.

FIG. 10 shows an alternative three dimensional non-knitted wire structure 20 as used in Comparative Example C which comprises a packed cylindrical array of intermeshing cylindrical elements 21, one of which is shown in FIGS. 8 and 9.

Element 21 is composed of double "S"-shaped adjacent opposed portions 22 which are connected end to end to constitute a helical looped wire 23. Wire 23 has a carrier cross-section (not shown) and eds 24 (only one shown). Each double "S"-shaped portion 22 defines two interstices 25 of a family and two opposed adjacent portions 22 define an intervening interstice 26 of a different family. The directions of the shortest pathways through interstices 25 and 26 are at least approximately orthogonal being respectively parallel to or transverse of the axis of element 21.

To make structure 20, a number of elements 21 are arranged into a cylindrical bundle and then metal filaments 27 are passed tightly around the bundle and tied by knots 28 whereupon filaments 27 keep wire structure 20 form-stable. Form stability is further enhcnaced by washcoating wire structure 20.

The invention is also illustrated by the following Examples of which Examples A to C are comparative.

EXAMPLE 1

Figure 1:
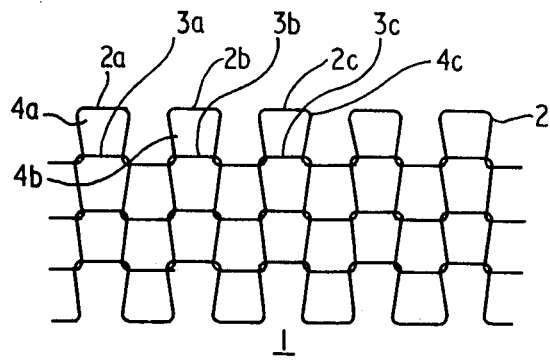
FIG. 1 is a plan of a two dimensional piece of knitted wire cloth used in making the wire structure.
Figure 3:
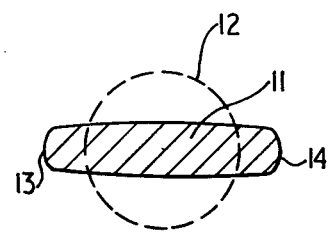
FIG. 3 is a section (shown on a larger scale) of a wire used in making the cloth shown in FIG. 1.
Figure 2:
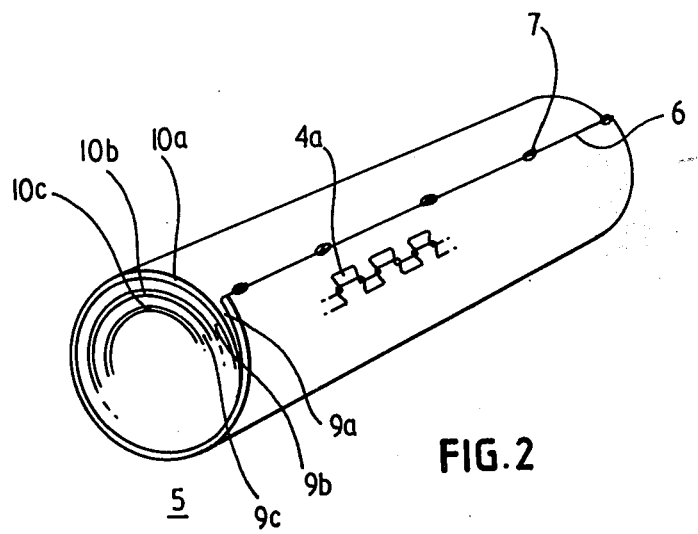
FIG. 2 is a diagrammatic perspective view of a compressed three dimensional wire structure made using a cloth of the kind shown in FIG. 1.

Example 1 illustrates the manufacture of a catalyst support and of a supported catalyst system. It also illustrates how the catalyst systems may be assembled and used in a vertical cylindrical trickle feed reactor. A cylindrical wire of diameter 0.254 mm made from stainless steel 304 (as designated by the Americal Iron and Steel Institute and which contains 19% by weight of chromium) was flattened by rolling and knitting into a cloth as shown in FIG. 1, then rolled, knotted, compressed radially inwardly and annealed to produce a cylindrical structure comprising intermeshing knitted layers as shown in FIG. 2. Clyindrical structures were made in which the total volumes of the interstices were 70%, 80%, 90% and 94% of the volume of the compressed structure.

To convert the structures to moiety-bearing catalyst supports the structures were heated to 1000° C. to generate a chromium oxide moiety, then cooled and immersed in a saturated solution of sodium aluminate whereupon a layer of gibbsite deposited. The structures where then dried overnight at 180° C. and fired to 540° C. to convert the gibbsite to $\gamma$-alumina so forming the moiety bearing catalyst support. Adhesion of the alumina to the oxidised wire was good in that there was no evidence of the alumina washcoat cracking or lifting. Similarly good adhesion is obtained if the wire is made from 'Fecralloy' instead of stainless steel 504. 'Fecralloy' is a ferritic steel containing aluminium. The amount of aluminium washcoat deposited on the oxidised wire is specified in Table 1.

TABLE 1

| % Interstitial Volume* | Weight of washcoat per gramme of oxidised wire |
|---|---|
| 70 | 0.1 g |
| 80 | 0.05 g |
| 90 | 0.1 g |
| 94 | 0.1 g |

*Volume of interstices expressed as a percentage of the total volume of the compressed structure To convert a support into a catalyst system, a catalyst component was applied to the support by impregnating the washcoat on the structure with a solution of a metal compound which on drying and firing decomposed to generate the catalyst component. Various alternative solutions include:

(a) aqueous potassium palladium nitrate which generates palladium,
(b) aqueous ruthenium acetate which generated ruthenium,
(c) aqueous copper nitrate which generated copper,
(d) a mixture of aqueous copper nitrate and chromic acid which generates copper chromite and
(e) aqueous aluminium sulphate which remains as aluminium sulphate.

The completed catalyst systems were cylindrical and each had a total volume of 100 cm$^{-3}$.

A standard procedure for using the catalyst systems was established. In the standard procedure one of the catalyst systems was loaded into a vertical cylindrical trickle feed reactor and liquid reactant was fed into the top of the reactor and allowed to trickle through the catalyst system. Gaseous reactant (or inert gas) was either pumped into the top of the reactor (ie standard co-current procedure) or into the bottom of the reactor (ie standard counter-current procedure). The results obtained by using the standard procedure under various conditions and with various catalysts systems are discussed in the following Examples. Unless otherwise stated, the interstitial volume of the structures used in the standard procedure was 90%.

EXAMPLES 2 TO 8 AND COMPARATIVE EXAMPLE A

These Examples illustrate the importance of a high interstitial volume in the wire structure.

In Examples 2, 3 and 4 crotonaldehyde was hydrogenated to n-butyraldehyde using the standard counter-current procedure and one of three alternative catalyst systems of different interstitial volume as specified in Table 2. The crotonaldehyde was fed at a flow rate of 75 cm$^3$/hr and the hydrogen was fed at a flow rate of 463 cm$^3$ min. The temperature in the column was maintained at just above ambient (about 20+/−5° C.) and the pressure was atmospheric. The conversions of crotonaldehyde achieved are shown in Table 2.

For the purposes of Comparative Example A, the standard co-current procedure was modified by using a conventional Harshaw pelletised copper chromite catalyst instead of a catalyst system made according to Example 1. The flow rates of crotonaldehyde and hydrogen were 300 cm$^3$/hr and 1850 cm$^3$/min respectively. Serious flooding and gas canalisation occurred and no discernable reaction occurred at just above ambient temperature. Little improvement was achieved by raising the temperature to 50° C.

In Examples 5 to 8 n-butyraldehyde was hydrogenated to n-butanol using the standard co-current procedure and one of the four alternative catalyst systems of different interstitial volumes as specified in Table 2 and impregnated with ruthenium to an extent of 0.8 g ruthenium/100 cm$^3$ of catalyst support. The flow rates of n-butyraldehyde and hydrogen were 30 cm$^3$/hr and 200 cm$^3$min respectively and the temperature and pressure maintained within the reactor was 140° C. and 1600 kPa. No flooding or gas canalisation occurred and as a result extremely high conversions and selectivities were achieved for this reaction.

COMPARATIVE EXAMPLE B

Comparative Example B illustrates the importance of structure which promotes substantial transverse flow. In Comparative Example B, the procedure of Example 5 to 8 was repeated except that instead of a catalyst system comprising an intermeshing wire structure, there was used a catalyst system which prevented transverse flow by comprising a support containing cylindrical spirally rolled interstitial and impermeable layers of the type designed for use in supports for catalysts used in the purification of exhaust gases from gasoline engines. The structure was made by lying a corrugated stainless steel foil on a flat impermeable foil to form what was essentially a two-dimensional two-foil sandwich. The sandwich was then spirally rolled and its loose edge was welded to the remainder of the roll so as to provide a form-stable three dimensional cylindrical structure analogous to that illustrated in FIG. 2 of the drawings. The structure contained longitudinal interstices defined partly by a portion of the flat foil and partly be a corrugation which abutted the flat foil. Accordingly the direction of the pathways through the interstices were all parallel and any significant transverse flow was prevented by the flat foil. The interstitial volume of structure was 88% of the total volume of the structure. The structure was washcoated and impregnated with ruthenium as for Examples 5 to 8 and then used in the hydrogenation of n-butyraldehyde.

The results are shown in Table 2.

EXAMPLES 9 AND 10

Example 6 was repeated using catalyst components which were copper metal (Example 9) or copper chromite (Example 10) instead of ruthenium metal. The copper metal component comprised 10% of the weight of the catalyst system. The copper chromite was used in an amount such that the catalyst system comprised 10% (by weight of the washcoat) of copper species and 10% (by weight of the washcoat) of chromium species. The results are shown in Table 2 and then demonstrate that the usefulness of the catalyst supports is not confined to precious metal components.

TABLE 2

| Example | Catalyst | % Interstitial Volume | % Selectivity to n-isomer | % Conversion to n-butyraldehyde or n-butanol |
|---|---|---|---|---|
| 2 | Palladium | 90 | — | 46.5 |
| 3 | Palladium | 80 | — | 8.1 |
| 4 | Palladium | 70 | — | 0.6 |
| A | Copper Chromite | About 30 | — | 0.3 |
| 5 | Ruthenium | 94 | 97.0 | 92.4 |
| 6 | Ruthenium | 90 | 98.1 | 95.5 |
| 7 | Ruthenium | 80 | 93.4 | 98.7 |
| 8 | Ruthenium | 70 | 90.0 | 92.6 |
| B | Ruthenium | 88 (Spiral structure) | 91.5 | 42.2 |
| 9 | Copper | 90 | 98.2 | 93.6 |
| 10 | Copper Chromite | 90 | 98.8 | 73.5 |

COMPARATIVE EXAMPLE C

Example 2 was repeated except that the catalyst system comprised a non-knitted wire structure composed of a bundle of helical lengths of 'Fecralloy' wire of circular cross-section as illustrated by FIGS. 8 to 10 instead of the flattened wire structure illustrated in FIGS. 1, 2, 3, 5 6 and 7. The results are shown in Table 3 and they illustrate the clear superiority of the knitted structure.

TABLE 3

| Example | Structure | % Conversion to n-butyraldehyde |
|---|---|---|
| 2 | knitted flattened wire | 46.5 |
| C | helical circular wire | 30.1 |

EXAMPLE 11

A wire structure having an interstitial volume of 90% was made as in Example 1. The structure was washcoated and then dipped into a colloidal solution of silica whereupon a layer of silica was deposited on the washcoat. Finally ruthenium metal was applied to the silica using the impregnation and firing technique of Example 1.

The catalyst was next used in the hydrogenation of n-butyraldehyde to n-butanol following the procedure of Example 6. A selectivity of 93% was achieved.

This Example demonstrates that silica is a good catalyst-bonding moiety which would be valuable for use in bonding catalyst components which would react with an alumina washcoat.

EXAMPLES 12 AND 13

The procedure of Example 2 was repeated using catalyst systems comprising amounts of palladium catalyst. The results are shown in Table 4.

TABLE 4

| Example | Pd content as wt % of weight of impregnated washcoat | % Conversion to n-butyraldehyde |
|---|---|---|
| 2 | 2 | 46.5 |
| 12 | 1 | 18.5 |
| 13 | 0.5 | 4 |

Clearly reducing the amount of palladium adversely affects the efficiency of the process.

EXAMPLES 14 TO 17

Example 2 was repeated using increasing flow rates as specified in Table 5. The results shown in Table 5 demonstrate that slower flow rates favour higher conversions and for this reason they are preferable. However slow flow rates cause flooding of close packed catalyst systems and so hitherto their benefits have been inaccessible in commercial processes.

TABLE 5

| Example | Flow Rate of Crotonaldehyde cm³/hr | Flow Rate of Hydrogen cm³/min | % Conversion to n-butyraldehyde |
|---|---|---|---|
| 2 | 75 | 463 | 46.5 |
| 14 | 150 | 925 | 22 |
| 15 | 300 | 1233 | 11 |
| 16 | 300 | 1850 | 6 |
| 17 | 300 | 2467 | 5 |

The remaining Examples demonstrate the versatility of the catalyst systems by illustrating the wide variety of other reactions in which they can be used.

EXAMPLES 18 TO 23

2-ethylhexenal (commonly known as 2-ethyl-3-propylacrolein or EPA) was hydrogenated to 2-ethyl hexanol using the standard co-current procedure and flow rates for EPA and hydrogen which were 30 cm³/hr and 400 cm³/min respectively. The temperatures and pressures used together with the results obtained are shown in Table 6.

TABLE 6

| Example | Catalyst | Temperature °C. | Pressure kPa | Selectivity % | Conversion % |
|---|---|---|---|---|---|
| 18 | Palladium | 150 | 3000 | 95.4 | 100 |
| 19 | Ruthenium | 120 | 1500 | 93.8 | 21.4 |
| 20 | Ruthenium | 120 | 3000 | 98.2 | 58.8 |
| 21 | Ruthenium | 140 | 1500 | 96.2 | 59.9 |
| 22 | Ruthenium | 160 | 1500 | 97.0 | 85.0 |

TABLE 6-continued

| Example | Catalyst | Temperature °C. | Pressure kPa | Selectivity % | Conversion % |
|---|---|---|---|---|---|
| 23 | Ruthenium | 160 | 3000 | 94.9 | 98.8 |

EXAMPLES 24 AND 25

Dodecaldehyde was hydrogenated to dodecanol using a ruthenium catalyst in the standard co-current procedure. The flow rates of dodecaldehyde and hydrogen were 30 cm³/hr and 200 cm³/min respectively and a pressure of 1500 kPa was used. The temperatures used and the results obtained are shown in Table 7.

TABLE 7

| Example | Temperature °C. | Selectivity % | Conversion % |
|---|---|---|---|
| 24 | 140 | 95.3 | 97.2 |
| 25 | 150 | 94.9 | 98.6 |

EXAMPLES 26 TO 36

Citral was hydrogenated to a product consisting of four derivatives as set out in Table 7. The selectivities shown in Table 7 relate to the total four component product. The standard co-current procedure was used employing either a palladium or ruthenium catalyst component at various temperatures and pressures all of which are specified in Table 8. The flow rates of citral and hydrogen were 30 cm³/hr and 300 cm³/min. Citral is believed to be a mixture of the geometric isomers I and II namely geranial (trans citral) and neral (cis citral) respectively. I and II

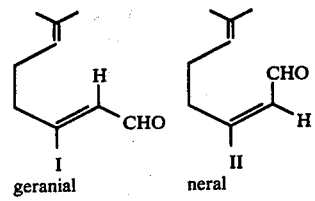

I  geranial      II  neral probably exist as tautomeric isomers III and IV. Not suprisingly, the product of

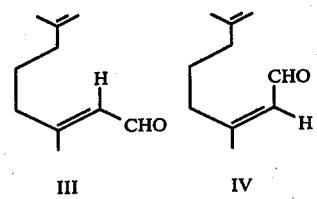

III            IV hydrogenation is a mixture in which one or more of citronellal, citronellol, 3,7-dimethyloctan-1-al or 3,7-dimehtyloctan-1-ol predominate. The results are shown in Table 7 which indicates how the choice of conditions can be used to vary the composition of the product.

TABLE 8

| Eg | Catalyst | Temp °C. | Pressure kPa | C-al** % by wt | C-ol** % by wt | *DMAL % by wt | *DMOL % by wt | Selectivity % | Conversion % |
|---|---|---|---|---|---|---|---|---|---|
| 26 | Palladium | 80 | 1550 | 36.9 | 1.2 | 38.0 | 2.0 | 87.4 | 84.3 |
| 27 | Palladium | 100 | 1550 | 32.5 | 1.0 | 38.4 | 3.5 | 85.5 | 88.0 |
| 28 | Palladium | 140 | 1550 | 3.9 | 0 | 75.2 | 16.2 | 100 | 100 |

TABLE 8-continued

| Eg | Catalyst | Temp °C. | Pressure kPa | C-al** % by wt | C-ol** % by wt | *DMAL % by wt | *DMOL % by wt | Selectivity % | Conversion % |
|---|---|---|---|---|---|---|---|---|---|
| 29 | Palladium | 140 | 3100 | 2.5 | 0 | 64.6 | 29.0 | 96.1 | 100 |
| 30 | Palladium | 180 | 1550 | 15.4 | 1.0 | 46.7 | 19.1 | 82.2 | 100 |
| 31 | Ruthenium | 140 | 1550 | 6.8 | 13.3 | 0 | 21.2 | 88.1 | 68.8 |
| 32 | Ruthenium | 160 | 1550 | 0.9 | 16.1 | 0 | 49.5 | 70.1 | 99.6 |
| 33 | Ruthenium | 180 | 1550 | 0.5 | 27.2 | 0 | 30.1 | 61.6 | 100 |
| 34 | Ruthenium | 200 | 2050 | 0.6 | 14.8 | 0 | 36.6 | 57.5 | 99.2 |
| 35 | Ruthenium | 140 | 3100 | 5.4 | 17.3 | 0 | 16.4 | 89.6 | 63.8 |
| 36 | Ruthenium | 200 | 3100 | 0 | 1.5 | 0 | 46.6 | 54.4 | 100 |

*% Percent by weight of total mixture produced by hydrogenation
**C-al is Citronellal
C-ol is Citronellol
DMAL is 3,7-dimethyloctan-1-al
DMOL is 3,7-dimethyloctan-1-ol

EXAMPLES 37 TO 41

Benzaldehyde was hydrogenated to benzyl alcohol using a palladium catalyst and the standard co-current procedure. The benzaldehyde and hydrogen flow rates were 30 cm$^3$/hr and 165 cm$^3$/min and the temperatures and pressures used together with the results are shown in Table 9.

TABLE 9

| Example | Temperature °C. | Pressure kPa | Selectivity % | Conversion % |
|---|---|---|---|---|
| 37 | 60 | 1500 | 91.1 | 79.0 |
| 38 | 60 | 3000 | 88.4 | 34.4 |
| 39 | 80 | 1500 | 90.1 | 99.7 |
| 40 | 80 | 3000 | 92.1 | 92.6 |
| 41 | 120 | 1500 | 87.4 | 98.1 |

EXAMPLES 42 TO 50

4-methyl-3-penten-2-one (commonly known as mesityl oxide) was hydrogenated to a mixture of methyl isobutyl ketone (MIBK) and methyl isobutyl carbonol (MIBC) using either a palladium or ruthenium catalyst in the standard co-current cm$^3$/hr and 300 cm$^3$/min. The temperatures and pressures used are shown in Table 10.

TABLE 10

| Example | Catalyst Component | Temperature °C. | Pressure kPa | % by wt MIBK | % by wt MIBC | % Selectivity to MIBK & MIBC | % Conversion |
|---|---|---|---|---|---|---|---|
| 42 | Palladium | 140 | 414 | 95.3 | 0.4 | 96.4 | 99.2 |
| 43 | Palladium | 160 | 414 | 97.0 | 1.4 | 98.8 | 00.6 |
| 44 | Palladium | 160 | 1550 | 95.9 | 0.3 | 96.7 | 99.5 |
| 45 | Palladium | 180 | 414 | 92.4 | 95.0 | 97.9 | |
| 46 | Ruthenium | 140 | 414 | 64.6 | 11.8 | 93.0 | 82.2 |
| 47 | Ruthenium | 160 | 414 | 41.2 | 43.5 | 85.8 | 98.7 |
| 48 | Ruthenium | 180 | 414 | 48.1 | 40.0 | 93.1 | 94.7 |
| 49 | Ruthenium | 140 | 1550 | 11.3 | 81.4 | 92.8 | 99.9 |
| 50 | Ruthenium | 150 | 1550 | 22.0 | 67.1 | 92.3 | 96.5 |

EXAMPLES 51 TO 60

Benzene in Examples 51 to 54 and toluene in Examples 55 to 60 were hydrogenated using a ruthenium catalyst and the standard co-current procedure. The temperatures and pressures used are specified in Table 11 and the flow rates were:

| Examples 51 to 54: | Benzene | 30 | cm$^3$/hr |
| | Hydrogen | 566 | cm$^3$/min |
| Examples 55 to 59: | Toluene | 30 | cm$^3$/hr |
| | Hydrogen | 480 | cm$^3$/min |

The results are shown in Table 11.

EXAMPLE 61

Cyclododecatriene dissolved in an equal amount by weight of heptane was hydrogenated using a palladium catalyst and the standard co-current procedure using the following conditions:

| Temperature | 140° C. |
| Pressure | 1600 kPa |
| Cyclododecatriene flow rate | 30 cm$^3$/hr |
| Hydrogen flow rate | 122 cm$^3$/min |

A 100% conversion of the triene and a 95% selectivity to cyclododecane were achieved.

TABLE 11

| Example | Temperature °C. | Pressure kPa | Selectivity % | Conversion % |
|---|---|---|---|---|
| 51 | 100 | 1500 | 88.3 | 99.8 |
| 52 | 80 | 1500 | 95.0 | 99.9 |
| 53 | 60 | 1500 | 98.3 | 100 |
| 54 | 60 | 667 | 96.7 | 100 |
| 55 | 80 | 1500 | 99.2 | 99.9 |
| 56 | 100 | 1500 | 99.2 | 97.3 |
| 57 | 120 | 2000 | 98.2 | 100 |
| 58 | 140 | 2000 | 93.6 | 99.7 |
| 59 | 160 | 2000 | 90.7 | 99.8 |
| 60 | 180 | 2000 | 69.9 | 99.8 |

EXAMPLES 61 AND 62

Ethanol or propanol were dehydrated by means of an aluminium sulphate catalyst component in the standard co-current procedure using nitrogen as an inert gas feed. The weight of aluminium sulphate used was 10% by weight of the washcoat. The flow rate of the alcohol and inert gas were 30 cm$^3$/hr and 200 cm$^3$/min respectively and the temperature and pressure was 300° C. and 500 kPa. The results are shown in Table 12.

TABLE 12

| Example | Alcohol | % by weight of product | | | % by wt unconv |
|---|---|---|---|---|---|
| | | Alkene | Ether | Water | |
| 61 | Ethanol | 16.7 Ethene | 2.4 diethyl-ether | 16.7 | 64 |
| 62 | Propanol | 13/4 Propene | 7.5 dipropyl-ether | 13.4 | 64 |

EXAMPLE 63

Crotanaldehyde was oxidised to crotonic acid using a palladium catalyst component in the standard co-current procedure in which the gas feed comprised argon containing 1% by weight of oxygen. The flow rates of crotonaldehyde and gas were 30 cm$^3$/hr and 6 l/min and the temperature and pressure were 50° C. and 770 kPa 6.4% by weight of the aldehyde was converted to crotonic acid.

EXAMPLE 64

The hydrogenolysis of benzaldehyde to toluene was performed using a ruthenium catalyst in the standard co-current procedure. The flow rates of benzaldehyde and hydrogen were 30 cm$^3$/hr and 350 cm cm$^3$/min and the temperature and pressure was 200° C. and 3100 kPa. 97.9% by weight of benzaldehyde was converted and the selectivity to toluene was 87.9%.

EXAMPLES 65 TO 68

To illustrate the sensitivity of the catalyst system, Example 6 was repeated except that various very dilute solutions of n-butyraldehyde in butanol were used instead of substantially undiluted butyraldehyde. The results are shown in Table 13. High conversions and selectivities were achieved despite the very open nature of wire structure.

TABLE 13

| Example | Conc by wt of butyraldehyde | Flow rate of butyraldehyde cm$^3$/hr | % Selectivity | % Conversion |
|---|---|---|---|---|
| 65 | 1% | 30 | 99.6 | 100 |
| 66 | 3% | 30 | 98.9 | 100 |
| 67 | 3% | *60 | 99.4 | 99.8 |
| 68 | 6% | *60 | 99.3 | 99.9 |

*Twice that used in Example 6.

We claim:

1. A three dimensional interstitial catalyst support suitable for use in a fluid/interstitial solid catalysed reaction wherein the support comprises a three dimensional wire interstitital structure composed of five or more superimposed intermeshing two dimensional layers of knitted wire interstitial cloth in which the volume of the interstices in the structure is from 60 to 98% of the total volume of the structure and in which the surface of the wire is provided with an oxide moiety suitable for bonding a catalyst component to the wire and which holds together adjacent portions of the layers of cloth to make the structure more form-stable.

2. A support as claimed in claim 1 wherein the volume of the interstices of the structure is 70 to 95% of the volume of the structure.

3. A support as claimed in claim 1 wherein the cloth comprises wire having a maximum transverse dimension of from 0.1 to 0.7 mm.

4. A support as claimed in claim 3 wherein the maximum dimension of each interstice of the structure is less than 10 times the maximum transverse dimension of the wire.

5. A support as claimed in claim 1 comprising interstices belonging to different families wherein the direction of the shortest pathway through an interstice of one family is inclined to the direction of the shortest pathway through an interstice of any other family.

6. A support as claimed in claim 1 wherein the structure comprises a rolled-up wire cloth.

7. A support according to claim 1 wherein the structure comprises wire having a non-circular cross-section.

8. A support according to claim 1 wherein the structure comprises wire made from an alloy containing a preferentially oxidisable component and the oxide moiety comprises a layer of oxide of a preferentially oxidisable metal beneath an outer layer of washcoated oxide.

9. A support according to claim 1 wherein the oxide moiety layer has a thickness of from 4 to 16 μm.

10. A support according to claim 1 wherein adjacent portions of the knitted wire are bonded together by cross-links consisting of oxide moiety.

11. A method for making a structure which is suitable for use in a catalyst support as claimed in claim 1 wherein the method comprises
 (a) arranging five or more layers of interstitial knitted wire cloth one on top of another,
 (b) compressing the arranged layers to a pre-determined volume,
 (c) annealing the compressed layers so that they become stable in a compressed state and
 (d) at some stage after step (a), securing the layers to produce a form-stable structure.

12. A method as claimed in claim 11 wherein the layers are arranged by rolling up a length of wire cloth.

13. A supported interstitial catalyst system comprising a catalyst component where the catalyst component is supported on an interstitial catalyst support as defined in claim 1.

14. A catalyst system according to claim 13 wherein the catalyst component comprises a precious metal.

15. A three dimensional interstitial catalyst support suitable for use in a fluid/interstitial solid catalysed reaction wherein
 (a) the support comprises a three-dimensional wire interstitial structure in which adjacent portions of wire are held together sufficiently to make the structure form-stable,
 (b) the surface of the wire is provided with a metal oxide suitable for bonding a catalyst component to the wire,
 (c) the interstices of the structure are defined by adjacent portions of wire and the interstices of the support are defined by adjacent portions of the metal oxide-bearing wire and
 (d) the volume of the interstices of the structure is from 60 to 98% of the structure, wherein the structure comprises an arrangement of five or more superimposed intermasking layers of interstitial knitted cloth.

* * * * *